US006875883B2

(12) United States Patent
Chorghade et al.

(10) Patent No.: US 6,875,883 B2
(45) Date of Patent: Apr. 5, 2005

(54) SYNTHESIS OF BENZONITRILES FROM SUBSTITUTED BENZALDEHYDE

(75) Inventors: Mukund S. Chorghade, Natick, MA (US); Mukund K. Gurjar, Pune Maharashtra (IN); Joseph Cherian, Kerala (IN)

(73) Assignee: Genzyme Corporation, Cambridge, MA (US)

( * ) Notice: Subject to any disclaimer, the term of this patent is extended or adjusted under 35 U.S.C. 154(b) by 123 days.

(21) Appl. No.: 10/439,286

(22) Filed: May 15, 2003

(65) Prior Publication Data

US 2003/0220504 A1 Nov. 27, 2003

Related U.S. Application Data

(60) Provisional application No. 60/392,833, filed on Jun. 27, 2002, provisional application No. 60/381,012, filed on May 15, 2002, provisional application No. 60/381,021, filed on May 15, 2002, provisional application No. 60/380,894, filed on May 15, 2002, provisional application No. 60/380,910, filed on May 15, 2002, provisional application No. 60/380,880, filed on May 15, 2002, provisional application No. 60/381,017, filed on May 15, 2002, provisional application No. 60/380,895, filed on May 15, 2002, provisional application No. 60/380,903, filed on May 15, 2002, provisional application No. 60/381,013, filed on May 15, 2002, provisional application No. 60/380,878, filed on May 15, 2002, and provisional application No. 60/380,909, filed on May 15, 2002.

(51) Int. Cl.[7] ............................................. C07C 253/12
(52) U.S. Cl. ....................................................... 558/315
(58) Field of Search ......................................... 558/315

(56) References Cited

U.S. PATENT DOCUMENTS

| 4,406,905 | A | 9/1983 | Zähner et al. |
|---|---|---|---|
| 5,554,753 | A | 9/1996 | O'Donnell et al. |
| 5,840,739 | A | 11/1998 | Bergeron, Jr. |
| 5,872,259 | A | 2/1999 | Reuter |
| 5,929,232 | A | 7/1999 | Jacobsen et al. |
| 6,083,966 | A | 7/2000 | Bergeron, Jr. |
| 6,159,983 | A | 12/2000 | Bergeron, Jr. |
| 6,383,233 | B1 | 5/2002 | Reuter |
| 6,428,583 | B1 | 8/2002 | Reuter |
| 6,521,652 | B1 | 2/2003 | Bergeron |
| 6,525,080 | B1 | 2/2003 | Bergeron |
| 6,559,315 | B1 | 5/2003 | Bergeron |
| 2003/0088105 | A1 | 5/2003 | Krich et al. |
| 2003/0225287 | A1 | 12/2003 | Chorghade et al. |
| 2003/0229231 | A1 | 12/2003 | Chorghade et al. |
| 2003/0236404 | A1 | 12/2003 | Gimi et al. |
| 2003/0236426 | A1 | 12/2003 | Chorghade et al. |
| 2003/0236434 | A1 | 12/2003 | Gimi et al. |
| 2003/0236435 | A1 | 12/2003 | Gimi et al. |
| 2004/0002613 | A1 | 1/2004 | Chorghade et al. |
| 2004/0006224 | A1 | 1/2004 | Chorghade et al. |
| 2004/0024224 | A1 | 2/2004 | Chorghade et al. |

FOREIGN PATENT DOCUMENTS

| DE | 30 02 989 A1 | 7/1981 |
|---|---|---|
| EP | 1 302 467 A2 | 4/2003 |
| GB | 1 292 170 | 10/1972 |
| WO | WO 94/11367 | 5/1994 |
| WO | WO 97/36885 | 10/1997 |
| WO | WO 00/01670 | 1/2000 |
| WO | WO 00/12493 A1 | 3/2000 |
| WO | WO 00/16763 | 3/2000 |
| WO | WO 01/51477 A1 | 7/2001 |
| WO | 03/097582 A2 * | 11/2003 |

OTHER PUBLICATIONS

Miller et al., Mild and efficient dehydration of oximes to nitriles mediated by the Burgess reagent; Synlett (2000), (8), pp. 1169–1171.*

Bergeron, R.J., et al., "The Desferrithiocin Pharmacophore," J. Med. Chem., 37: 1411–1417 (1994).

Bergeron, R.J., et al., "Effects of C–4 Stereochemistry and C–4' Hydroxylation on the Iron Clearing Efficiency and Toxicity of Desferrithiocin Analogues," J. Med. Chem., 42: 2432–2440 (1999).

Bergeron, R., et al., "Desazadesmethyldesferrithiocin Analogues as Orally Effective Iron Chelators," J. Med. Chem., 42:95–108 (1999).

Bergeron, R. et al., "Synthesis and Biological Evaluation of Naphthyldesferrithiocin Iron Chelators," J. Med. Chem., 39:1575–1581 (1996).

Bergeron, R. et al., "Evaluation of Desferrithiocin and Its Synthetic Analogues as Orally Effective Iron Chelators," J. Med. Chem., 34:2072–2078 (1991).

Bergeron, R. et al., "Evaluaton of the Desferrithiocin Pharmacophore as a Vector for Hydroxamates," J. Med. Chem., 42:2881–2886 (1999).

Bergeron, R. et al., "An Investigation of Desferrithiocin Metabolism," J. Med. Chem., 37:2889–2895 (1994).

(Continued)

Primary Examiner—Johann Richter
Assistant Examiner—Ebenezer Sackey
(74) Attorney, Agent, or Firm—Hamilton, Brook, Smith & Reynolds, PC

(57) ABSTRACT

There is a significant demand for organic nitriles, based on their versatility in reactions. Compounds prepared from nitriles have properties including superoxide inhibition, ferrielectric liquid crystal dopant, antipicornaviral agents, anti-inflammatory agents, anti-asthma agents, and fibringoen antagonists. The present invention discloses a facile synthesis for 2,4-dihydroxybenzonitrile, and ethers and diethers thereof, from 2,4-dihydroxybenzaldehyde or 2,4-dimethoxybenzaldehyde. The present invention also discloses a method of preparing a class of iron chelating agents related to desferrithiocin, all of which contain a thiazoline ring. In this method, 2,4-dihydroxybenzonitrile is condensed with (S)-2-methylcysteine.

6 Claims, No Drawings

OTHER PUBLICATIONS

Bergeron, R. et al., "A Comparative Study of the Iron–Clearing Properties of Desferrithiocin Analogues with Desferrioxamine B in a *Cebus* Monkey Model," *Blood*, 81(8):2166–2173 (1993).

Bergeron, R. et al., "Pharmacokinetics of Orally Administered Desferrithiocin Analogs in *Cebus Apella* Primates," *Drug Metabolism and Disposition*, 27(12):1496–1498 (1999).

"Addition to Carbon–Hetero Multiple Bonds" In *Advanced Organic Chemistry*, by Jerry March (Wiley Interscience), Ch. 16, pp. 906–907 (1992).

Mulqueen, G. C., et al., "Synthesis of the Thiazoline–based Siderophore (S)–Desferrithiocin," *Tetrahedron*, 49(24):5359–5364 (1993).

O'Donnell, M. J. et al., "α–Methyl Amino Acids by Catalytic Phase–Transfer Aklylations," *Tetrahedron Letters*, 23(41):4259–4262 (1982).

\* cited by examiner

SYNTHESIS OF BENZONITRILES FROM SUBSTITUTED BENZALDEHYDE

RELATED APPLICATIONS

This application claims the benefit of U.S. Provisional Application Nos. 60/381,012, 60/381,021, 60/380,894, 60/380,910, 60/380,880, 60/381,017, 60/380,895, 60/380,903, 60/381,013, 60/380,878 and 60/380,909, all of which were filed May 15, 2002. This application also claims the benefit of U.S. Provisional Application Ser. No. 60/392,833, filed Jun. 27, 2002. The entire teachings of the above-referenced applications are incorporated herein by reference.

BACKGROUND OF THE INVENTION

Nitrile-containing compounds are highly in demand because nitrile moieties are versatile reagents for organic synthesis as exemplified in their applications in the preparation of thiazoles, chrial 2-oxazolines, tetrazoles, 1,2-diarylimidazoles, triazolo[1,5-c]pyrimidines, and benzamidines. Compounds prepared from nitriles have properties including superoxide inhibition, ferrielectric liquid crystal dopants, antipicornaviral agents, anti-inflammatory agents, anti-asthma agents, and fibrinogen antagonists.

The use of nitriles in the preparation of thiazoles, or when reduced, thiazolines and thiazolidines, is of particular interest. Compounds such as desferrithiocin and structural analogues contain a thiazoline ring, and these compounds represent an advance in iron chelation therapy for subjects suffering from iron overload diseases. Present therapeutic agents such as desferrioxamine require parenteral administration and have a very short half-life in the body, so that patient compliance and treatment cost are serious problems for subjects receiving long-term chelation therapy. Desferrithiocin and related compounds are effective when orally administered, thereby reducing patient compliance issues.

Unfortunately, 2,4-dihydroxybenzonitrile, which is a precursor to the potent, less toxic form of desferrithiocin known as 4'-hydroxydesazadesferrithiocin, remains a synthetic challenge. At this time, 2,4-dihydroxybenzonitrile is not commercially available and the related 2,4-dimethoxybenzonitrile is expensive. Therefore, there is a need for novel methods of producing 2,4-dihydroxybenzonitrile (or ethers thereof) at a reasonable cost.

SUMMARY OF THE INVENTION

The present invention includes a method of preparing a substituted benzonitrile represented by Structural Formula (I):

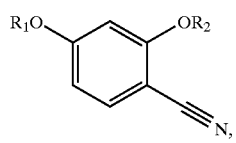

wherein $R_1$ and $R_2$ are each independently —H, a substituted or unsubstituted alkyl group, or a substituted or unsubstituted aryl group;

comprising the steps of:

a.) reacting hydroxylamine or a protected derivative or a salt thereof and a disubstituted benzaldehyde represented by Structural Formula (II):

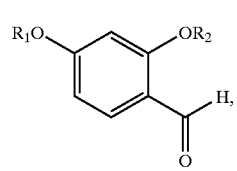

wherein $R_1$ and $R_2$ are as defined above, thereby forming a substituted benzaldoxime represented by Structural Formula (III):

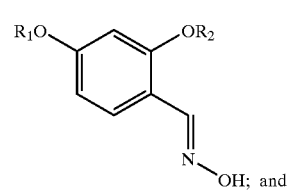

b.) reacting the substituted benzaldoxime with diphosphorus pentoxide, thereby forming the substituted benzonitrile represented by Strucutural Formula (I).

In another embodiment, the present invention is a method of preparing a compound represented by Structural Formula (IV):

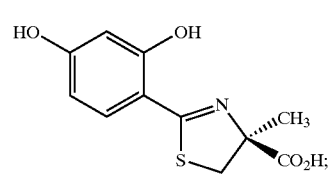

comprising the steps of:

a.) reacting hydroxylamine or a protected derivative or a salt thereof and a disubstituted benzaldehyde represented by Structural Formula (II):

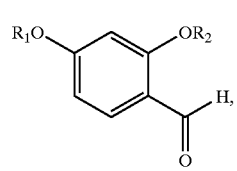

wherein $R_1$ and $R_2$ are each independently —H, a substituted or unsubstituted alkyl group, or a substituted or unsubstituted aryl group; thereby forming a substituted benzaldoxime represented by Structural Formula (III):

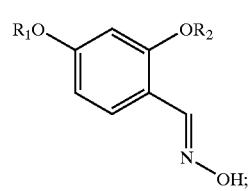

b.) reacting the substituted benzaldoxime with diphosphorus pentoxide, thereby forming the substituted benzonitrile represented by Strucutural Formula (I):

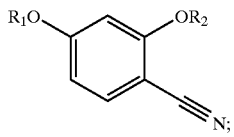 (I)

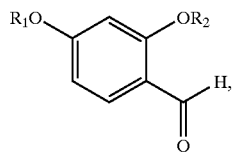 (II)

c.) if R₁ and R₂ are not each —H, reacting the product of step (b.) with a deprotecting agent, thereby forming 2,4-dihydroxybenzonitrile; and d.) coupling (S)-2-methylcysteine with 2,4-dihydroxybenzonitrile, thereby forming the compound represented by Structural Formula (IV).

Advantages of the present invention include the facile synthesis of 2,4-dihydroxybenzonitrile, or an ether or diether thereof, from 2,4-dihydroxybenzoic acid, an inexpensive and readily available starting material. 2,4-Dihydroxybenzonitrile prepared by the method of the present invention can be coupled to (S)-2-methylcysteine to form 4'-hydroxydesazadesferrithiocin, also referred to as 4,5-dihydro-2-(2,4-dihydroxyphenyl)-4-methylthiazole-4 (S)-carboxylic acid, an iron chelating agent.

DETAILED DESCRIPTION OF THE INVENTION

A useful and efficient method of preparing 2,4-dihydroxybenzonitrile, or an ether or diether thereof, involves reacting 2,4-dihydroxybenzaldehyde or a diether thereof, such as 2,4-dimethoxybenzaldehyde, with hydroxylamine or a protected derivative or a salt thereof, to form an oxime. The oxime is typically dehydrated with diphosphorus pentoxide to form 2,4-dihydroxybenzonitrile or an ether or diether thereof. For ethers and diethers of 2,4-dihydroxybenzonitrile, additional steps may be desirable to cleave the ether moieties and obtain 2,4-dihydroxybenzonitrile.

In examples where R₁ and R₂ are each —H, R₁ and R₂ can be protected by protecting groups, prior to reaction of the aldehyde moiety. A preferred protecting group is a substituted or unsubstituted alkyl group such as a methyl group. Protecting groups can be added, for example, by reacting 2,4-dihydroxybenzaldehyde, a base, and CH₃—Z, where Z is a leaving group (e.g., tosylate, halide such as chloride or bromide) in a polar, aprotic solvent. Suitable bases include sodium hydroxide, potassium hydroxide, sodium methoxide, potassium methoxide, sodium ethoxide, potassium ethoxide, sodium carbonate, calcium carbonate, cesium carbonate, and potassium carbonate. Polar, aprotic solvents include acetone, acetonitrile, dimethylformamide, dioxane, ethyl acetate, ethyl ether, tetrahydrofuran, and hexamethylphosphoramide. Other suitable protecting group can be found in "Protective Groups in Organic Synthesis," by Peter G. M. Wuts and Theodora W. Greene, Wiley-Interscience, 1990, the teachings of which are incorporated herein by reference in their entirety.

The first step of the reaction involves reacting a compound represented by Structural Formula (II):

with hydroxylamine or a protected derivative or a salt thereof (e.g., hydroxylammonium sulfate), to form an oxime. The hydroxyl moiety of hydroxylamine can be protected as benzyl ether, t-butyl ether, 2,6-dichlorobenzyl ether, 2-bromobenzyl ether, and 3,5-dibromobenzyl ether. In a preferred embodiment, R₁ and R₂ are each independently a substituted or unsubstituted alkyl group or a substituted or unsubstituted aryl group. In a more preferred embodiment, R₁ and R₂ are each methyl. Typically, the compound represented by Structural Formula (II) is reacted with one or more equivalents (e.g., about 1 to about 10 equivalents, about 2 to about 8 equivalents, about 3 to about 6 equivalents) of hydroxylamine. Suitable conditions for reacting an aldehyde and hydroxylamine can be found, for example, on pages 906–907 of "Advanced Organic Chemistry, Fourth Edition," by Jerry March, Wiley-Interscience, 1992, and references therein, all of which are incorporated by reference. In reactions of an aldehyde and hydroxylamine, the pH of the solvent (e.g., water or a mixture of water and a water-miscible organic solvent) is preferably about 4, or is in a range from about 3.5 to about 4.5, about 3 to about 5, or about 2 to about 6.

The second step of the reaction involves reacting the oxime with diphosphorus pentoxide. Typically, P₂O₅ is heated with the oxime for 1 or more hours (e.g., about 1 to about 12 hours, about 2 to about 8 hours, about 3 to about 6 hours) at room temperature or greater (e.g., about 20° C. to about 200° C., about 40° C. to about 150° C., about 60° C. to about 100° C.). One or more equivalents, such as about 1 to about 6 equivalents, about 1.5 to about 5 equivalents, or about 2 to about 4 equivalents, of P₂O₅ are generally required for the reaction.

Following the second step, when R₁ and R₂ are not each —H, it is often advantageous to remove R₁ and R₂, otherwise known as deprotecting the ether groups of a nitrile product. Typically, the product of the second step is isolated before proceeding with deprotecting. Deprotecting an ether group can be achieved by reacting a protected ether with a deprotecting agent. Preferred deprotecting agents include boron trihalides such as boron trifluoride, boron trichloride, and boron tribromide. Additional deprotecting methods can be found in "Protective Groups in Organic Synthesis," which was previously incorporated by reference.

Cysteine or a 2-alkylcysteine such as (S)-2-methylcysteine can be coupled with 2,4-dihydroxybenzonitrile, or an ether or diether thereof. In a preferred embodiment, (S)-2-methylcysteine is coupled to 2,4-dihydroxybenzonitrile to form 4,5-dihydro-2-(2,4-dihydroxyphenyl)-4-methylthiazole-4(S)-carboxylic acid (also known as 4'-hydroxydesazadesferrithiocin).

Syntheses of cysteine and cysteine derivatives suitable for coupling can be found in U.S. Application Nos. 60/381,012, 60/381,021, 60/380,894, 60/380,910, 60/380,880, 60/381,017, 60/380,895 and 60/380,903, filed May 15, 2002, and U.S. Application No. 60/392,833, filed Jun. 27, 2002; the entire teachings of which are incorporated herein by reference.

Typically, coupling of cysteine or a 2-alkylcysteine and a substituted benzonitrile includes converting the benzonitrile into a benzimidate. The benzimidate can be formed, for example, by reacting the benzonitrile with an alcohol such as methanol, ethanol, n-propanol, or isopropanol in the presence of an acid such as hydrochloric acid. The benzimidate is then reacted with the cysteine (or related compound) under basic conditions. Acceptable bases include dimethylamine, diethylamine, diphenylamine, trimethylamine, triethylamine, triphenylamine, diisopropylamine, diisopropylethylamine, 1,4-diazabicyclo [2.2.2.]octane (DABCO), 1,5-diazabicyclo [4.3.0]non-5-ene (DBN), and the like. The reaction between the benzimidate and the cysteine results in the thiazoline (or 4,5-dihydrothiazole) containing product. When forming the benzimidate from a hydroxylated benzonitrile (e.g., 2,4-dihydroxybenzonitrile), the hydroxyl groups are advantageously protected (e.g., with a substituted or unsubstituted alkyl or arylalkyl group such as a benzyl group). The protecting groups are subsequently cleaved, typically by catalytic hydrogenation.

Products synthesized by methods of the present invention can be purified by a method known in the art. For example, compounds of the present invention can be purified using emulsion crystallization.

The methods of the claimed invention can be used to manufacture other related desferrithiocin analogs and derivatives. Examples of such analogs include those described in U.S. Pat. Nos. 5,840,739, 6,083,966, 6,159,983, 6,521,652 and 6,525,080, to Raymond J. Bergeron, Jr., the contents of which are incorporated herein by reference. Additional examples can be found in PCT/US93/10936, PCT/US97/04666, and PCT/US99/19691, the contents of which are incorporated by reference.

An alkyl group is a hydrocarbon in a molecule that is bonded to one other group in the molecule through a single covalent bond from one of its carbon atoms. Alkyl groups can be cyclic or acyclic, branched or unbranched, and saturated or unsaturated. Typically, an alkyl group has one to about 24 carbons atoms, or one to about 12 carbon atoms. Lower alkyl groups have one to four carbon atoms and include methyl, ethyl, n-propyl, iso-propyl, n-butyl, sec-butyl and tert-butyl.

Aromatic (or aryl) groups include carbocyclic aromatic groups such as phenyl, p-tolyl, 1-naphthyl, 2-naphthyl, 1-anthracyl and 2-anthracyl. Aromatic groups also include heteroaromatic groups such as N-imidazolyl, 2-imidazole, 2-thienyl, 3-thienyl, 2-furanyl, 3-furanyl, 2-pyridyl, 3-pyridyl, 4-pyridyl, 2-pyrimidyl, 4-pyrimidyl, 2-pyranyl, 3-pyranyl, 3-pyrazolyl, 4-pyrazolyl, 5-pyrazolyl, 2-pyrazinyl, 2-thiazolyl, 4-thiazolyl, 5-thiazolyl, 2-oxazolyl, 4-oxazolyl and 5-oxazolyl.

Aromatic groups also include fused polycyclic aromatic ring systems in which a carbocyclic, alicyclic, or aromatic ring or heteroaryl ring is fused to one or more other heteroaryl or aryl rings. Examples include 2-benzothienyl, 3-benzothienyl, 2-benzofuranyl, 3-benzofuranyl, 2-indolyl, 3-indolyl, 2-quinolinyl, 3-quinolinyl, 2-benzothiazole, 2-benzooxazole, 2-benzimidazole, 2-quinolinyl, 3-quinolinyl, 1-isoquinolinyl, 3-quinolinyl, 1-isoindolyl and 3-isoindolyl.

Suitable substituents for alkyl groups include —OH, halogen (—Br, —Cl, —I and —F), —O(R'), —O—CO—(R'), —CN, —NO$_2$, —COOH, =O, —NH$_2$, —NH(R'), —N(R')$_2$, —COO(R'), —CONH$_2$, —CONH(R'), —CON(R')$_2$, —SH, —S(R'), and guanidine. Each R' is independently an alkyl group or an aryl group. Alkyl groups can additionally be substituted by a aryl group (e.g. an alkyl group can be substituted with an aromatic group to form an arylalkyl group). A substituted alkyl group can have more than one substituent.

Suitable substituents for aryl groups include —OH, halogen (—Br, —Cl, —I and —F), —O(R'), —O—CO—(R'), —CN, —NO$_2$, —COOH, =O, —NH$_2$, —NH(R'), —N(R')$_2$, —COO(R'), —CONH$_2$, —CONH(R'), —CON(R')$_2$, —SH, —S(R'), and guanidine. Each R' is independently an alkyl group or an aryl group. Aryl groups can additionally be substituted by an alkyl or cycloaliphatic group (e.g. an aryl group can be substituted with an alkyl group to form an alkylaryl group such as tolyl). A substituted aryl group can have more than one substituent.

Diphosphorus pentoxide is a dehydrating agent. Other dehydrating agents include acetic anhydride, ethyl orthoformate in an acidic solution, triphenylphosphine in carbon tetrachloride, trichloromethylchloroformate, methyl cyanoformate, ethyl cyanoformate, trifluoromethane sulfonic anhydride, P$_2$I$_4$, SeO$_2$, trichloroformyl chloride in triethylamine, and chloromethylene dimethylammonium chloride.

Boron trihalides are acceptable deprotecting agents (i.e., for hydrolysis of ethers) for use in the present invention. Other deprotecting agents include (CH$_3$)$_2$BBr, AlCl$_3$, (CH$_3$)$_3$SiI, SiCl$_4$/NaI, SiH$_2$I$_2$, LiI, NaI/BF$_3$, and (CH$_3$)$_3$SiCl/NaI.

EXAMPLE 1

2,4-Dimethoxybenzoic acid is reacted with hydroxylamine to form 2,4-dimethoxybenzaldoxime. 2,4-Dimethoxybenzaldoxime is reacted with diphosphorus pentoxide to form 2,4-dimethoxybenzonitrile. 2,4-Dimethoxybenzonitrile is reacted with boron trichloride to form 2,4-dihydroxybenzonitrile.

EXAMPLE 2

35 mg of R- and S-4,5-dihydro-2-(2,4-dihydroxyphenyl)-4-methylthiazole-4-carboxylic acid were dissolved in 1 ml of a mixture of 9% N-methyl-pyrrolidone, 9% v/v 2-hexanol, 10% v/v Rhodafac RE 610, 5% v/v Soprophor FL and 68% v/v water by heating to 50° C. in a 5 mL vial. After the product was completely dissolved, the microemulsion was cooled down to room temperature and agitated with a shaking machine (350 rpm). During two hours, no spontaneous crystallization was observed. The mixture was then seeded with two drops of a dilute, finely ground suspension of pure S-product crystals grown under similar conditions. After two hours of shaking, the resulting crystals were filtered off, washed with water and dried in a gentle nitrogen stream. The procedure yielded 5.4 mg (15.4%) of colorless crystals, with a greater than 90% purity of the S entantiomer.

EXAMPLE 3

4.00 g (S)-2-methylcysteine hydrochloride (23.3 mmol, 1.0 meq) and 3.14 g 2,4-dihydroxy benzonitrile (23.3 mmol, 1.0 meq) were suspended in 40 mL ethanol. After degassing this mixture with nitrogen (30 min) 4.95 g triethylamine (6.8 mL, 48.9 mmol, 2.05 meq) were added. The obtained suspension was heated under reflux in an atmosphere of nitrogen for 20 hours and then cooled to room temperature. From this suspension ethanol was evaporated under reduced pressure until an oil (20% of the initial volume) was obtained. This oil was dissolved in 50 mL water. The solution was adjusted to pH 7.5 with 1.20 ml 20% KOH and was extracted two times each with 20 mL methyl t-butyl ether (MTBE). The aqueous layer was separated, adjusted with 20% KOH to pH 11 and again extracted two times each with 20 mL MTBE. After separating the aqueous layer the pH was set with concentrated HCl to 7.5 and traces of MTBE were distilled off. Then the aqueous solution was acidified with 1.50 mL concentrated HCl to pH 1.5. The product precipitated. This suspension was stirred at 4° C. for 1 hour. Then the precipitate was filtered, washed two times each with 10 mL water (5° C.) and dried at 45° C. under vacuum. The reaction yielded 5.17 g (87.6%) of crude 4,5-dihydro-2-(2,4-dihydroxyphenyl)-4-methylthiazole-4 (S)-carboxylic acid product. $^1$H-NMR showed no significant impurity.

EXAMPLE 4

Synthesis of 2,4-Dihydroxy-benzonitrile

In a double walled reactor 50.0 g (0.362 mol, 1.0 meq) 2,4-dihydroxybenzaldehyde were added to 180 mL formic acid, which resulted in a brown suspension at room temperature. Then 45.8 g (0.673 mol, 1.8 meq) sodium formate were added over 2 min, and the temperature increased to 33° C. After the temperature decreased to 30° C., 35.6 g (0.217 mol, 1.2 meq) hydroxyl ammonium sulfate were added during 3 min to give a thick brown suspension which became a brown solution after stirring 10 min at 30–32° C. While heating the mixture to 100° C., crystallization occurred at 38° C. and stirring was interrupted. At 70° C. the reaction mixture became a thin suspension, which was easy to stir. This reaction mixture was stirred for 2 hours at 100° C. The color turned dark brown. TLC (silica gel 60 F254, acetone:n-hexane:water 20:20:1) showed an almost complete reaction. Formic acid (170 mL) was evaporated under reduced pressure (60° C., 10 mbar). The solid dark brown residue was stirred with 400 mL MTBE at 40° C. for 1 hour (incomplete dissolution). The insoluble residue (62.5 g) was filtered and washed two times each with 50 mL MTBE. To the mother liquor 10 g activated carbon (Norit CA 5) were added and this mixture was refluxed for 1 hour and filtered at 40° C. by Celite Super Hyflow (washing with 2×50 mL portions of MTBE). The MTBE-mother liquor was washed three times each with 100 mL water. After removing the water from this MTBE solution with azeotropic distillation (water separator) it was concentrated under reduced pressure to 20% of the starting volume and 500 mL toluene were added. Then the MTBE was distilled off under reduced pressure. During this process a brown residue began to precipitate, which was filtered. The toluene mother liquor was concentrated to 150 mL and 2,4-dihydroxybenzonitrile precipitated, which was filtered and washed two times each with 30 mL toluene. The pale tan product was dried under reduced pressure (45° C., 20 mbar). The reaction yielded 34.5 g of 2,4-dihydroxybenzonitrile (70.5%, purity 97% (HPLC)).

EXAMPLE 5

2,4-Dibenzyloxybenzonitrile (0.121 mol) was dissolved in 5.85 g (0.127 mol) ethanol and 19.4 ml 1,2-dimethoxyethane in a double walled reactor. This solution was cooled to −5° C., stirred and saturated with dry HCl gas over 5 hours at 0–3° C. The reaction mixture was stirred overnight at 2–4° C. under nitrogen. During this time, a product crystallized. The white crystals were filtered off, washed with 1,2-dimethoxyethane (5° C., three times each with 13 ml) and dried. A total of 30 of the protected ethyl benzimidate was isolated (Yield 88.4%, purity 98.9%).

The protected ethyl benzimidate described above was dissolved in methanol to generate a 10% solution and was catalytically hydrogenated at room temperature using 5% Pd/C as a catalyst. The reaction was completed after 8 hours. The solution was filtered and the solvent evaporated to yield the deprotected product as an orange-yellow solid. The reaction yielded 19.6 g (94%) of product.

In contrast, the formation of the imidate with 2,4 dihydroxybenzonitrile was a low yielding process, generating the desired product in only 20% yield and with less than desired purity.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of preparing a substituted benzonitrile represented by Structural Formula (I):

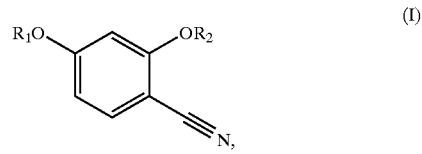

wherein $R_1$ and $R_2$ are each independently —H, a substituted or unsubstituted alkyl group, or a substituted or unsubstituted aryl group;

comprising the steps of:

a.) reacting hydroxylamine or a protected derivative or a salt thereof and a disubstituted benzaldehyde represented by Structural Formula (II):

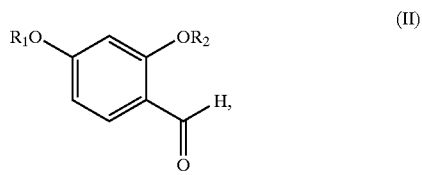

wherein $R_1$ and $R_2$ are as defined above, thereby forming a substituted benzaldoxime represented by Structural Formula (III):

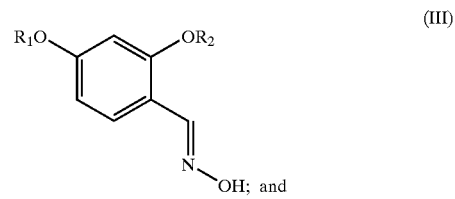

b.) reacting the substituted benzaldoxime with diphosphorus pentoxide, thereby forming the substituted benzonitrile represented by Strucutural Formula (I).

2. The method of claim 1, wherein $R_1$ and $R_2$ are each independently a substituted or unsubstituted alkyl or a substituted or unsubstituted aryl group.

3. The method of claim 2, wherein $R_1$ and $R_2$ are each a methyl group.

4. The method of claim 3, further comprising the step of reacting the product of step (b.) with a deprotecting agent, thereby forming 2,4-dihydroxybenzonitrile.

5. The method of claim 4, wherein the deprotecting agent is a boron trihalide.

6. The method of claim 5, wherein the boron trihalide is boron trichloride.

* * * * *